United States Patent [19]

Juguin et al.

[11] 4,395,580
[45] Jul. 26, 1983

[54] PROCESS FOR PRODUCING AN OLEFIN BY DECOMPOSITION OF THE CORRESPONDING ETHER

[75] Inventors: Bernard Juguin, Rueil-Malmaison; Jean Miquel, Paris; Michel Hellin, Andresy; Bernard Torck, Boulogne sur Seine, all of France

[73] Assignee: Institut Francais Du Petrole, Rueil-Malmaison, France

[21] Appl. No.: 316,376

[22] Filed: Oct. 29, 1981

[30] Foreign Application Priority Data

Oct. 29, 1980 [FR] France .................. 80 23183

[51] Int. Cl.³ .................. C07C 1/00; C07C 1/24
[52] U.S. Cl. .................. 585/639; 585/640
[58] Field of Search .................. 585/639, 640

[56] References Cited

U.S. PATENT DOCUMENTS

| | | | |
|---|---|---|---|
| 3,401,210 | 9/1968 | de Jongh et al. | 585/639 X |
| 4,006,198 | 2/1977 | Tosei et al. | 585/640 |
| 4,072,732 | 2/1978 | Hargis et al. | 585/639 |
| 4,072,733 | 2/1978 | Hargis et al. | 585/639 |
| 4,254,296 | 3/1981 | Manara et al. | 585/640 |
| 4,320,232 | 3/1982 | Volkamer et al. | 585/639 X |

Primary Examiner—Paul F. Shaver
Attorney, Agent, or Firm—Millen & White

[57] ABSTRACT

Process for producing very pure olefins of the formula

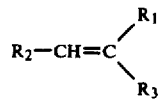

by decomposition of the corresponding ethers of formula

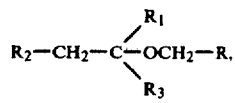

wherein $R_1$ and $R_3$ are selected from the group of the alkyl, arylalkyl aryl or alkylaryl radicals, R and $R_2$ being a hydrogen atom or a radical selected from said above mentioned group, in the presence of steam in a molar proportion from 2 to 8 times the ether amount and with the use of a catalyst comprising alumina to which is added 0.01 to 5% by weight of titanium or zirconium or hafnium as metal or as metal compound, said catalyst having a specific surface form 80 to 300 $m^2/g$.

22 Claims, No Drawings

PROCESS FOR PRODUCING AN OLEFIN BY DECOMPOSITION OF THE CORRESPONDING ETHER

BACKGROUND OF THE INVENTION

This invention concerns a process and a catalyst for producing very pure olefins of the formula

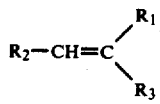

from the corresponding ethers of the formula

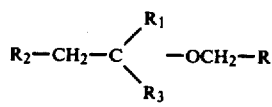

where R, $R_1$, $R_2$ and $R_3$, identical or different, are alkyl, arylalkyl, aryl or alkylaryl radicals, $R_2$ and R being optionally a hydrogen atom.

It is known that the olefinic hydrocarbons, when contacted with an acid such as sulfuric acid or with a solid having appropriate acidic properties, react with alcohols to produce ethers. The velocity of this reaction depends on the operating conditions (pressure, temperature, contact time, etc. ...) used for carrying out this reaction.

A judicious choice of these operating conditions makes it possible to effect the selective reaction, in an olefinic charge, of the olefins of formula

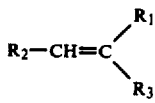

(i.e. having a tertiary carbon atom in the immediate vicinity of the double bond), with at least one primary alcohol of formula R—$CH_2OH$, so as to form tert-alkyl ethers, according to reaction (1) below.

These tert-alkyl ethers may in turn be decomposed, in the presence of a catalyst and under suitable operating conditions, to give, selectively, the alcohol and the starting olefin, also called tertiary olefin in the literature.

These two successive reactions have been used in the prior art for producing so-called tertiary olefins from an olefinic cut: Thus, processes for manufacturing tertiary olefins (isobutene, isopentene, etc. ...) of high purity, have been described, in the literature, based on the selective "extraction" of the tertiary olefins from an olefinic cut, i.e. the treatment of the tertiary olefin with an alcohol, taking advantage of the selectivity of reaction (1), whereby it is possible to obtain the corresponding tertiary ether:

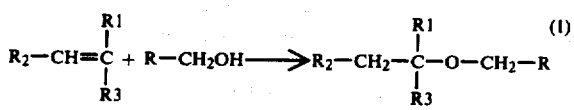

The desired so-called tertiary olefin is thus separated in the form of an ether, which is easily isolated, for example by distillation of the mixture withdrawn from the reaction zone, which mixture contains unreacted hydrocarbons, the excess of alcohol (generally a primary alcohol) and the formed ether.

The final step of the process is then the decomposition of the obtained ether into its starting constituents: the alcohol and the desired tertiary olefin. The alcohol may be recycled in order to be again reacted with the tertiary olefins of the fresh cut used as charge. Such a decomposition step is described, for example, in the U.S. Pat. No. 3,170,000, in the presence of a catalyst whose specific surface must be lower than 25 $m^2/g$, and in the British Pat. No. 1,176,620 wherein the operation is conducted in the presence of steam.

However, this type of decomposition reaction, up to now, was not sufficiently selective as a result of parasitic reactions taking place therewith and which decrease the yields of tertiary olefin and of recovered alcohol.

These parasitic reactions are particularly of the following types:
- the formed alcohol may react with itself while dehydrating, to produce an ether and water (for example dimethylether and water when the alcohol is methanol);
- the obtained olefin may dimerize, or even trimerize;
- the olefin may also be hydrated to the corresponding tertiary alcohol.

In view of the fact that the desired tertiary olefins form a very valuable raw material for the manufacture of derivatives (for example gasolines, alkylates, polymers and other chemical products), it is thus very important to obtain them in their highest possible degree of purity.

The catalysts used up to now for this reaction of decomposing tert-alkyl-ethers are not sufficiently selective since, in most cases, they favour the formation of dialkyl ethers by dehydration of the corresponding primary alcohols which have been formed. This parasitic reaction is the more favoured as the reaction temperature is the higher; in this connection it must be mentioned that many of the catalysts used require relatively high temperatures in order to have a sufficient activity.

This parasitic reaction results in a loss of alcohol and, consequently, in the requirement of fresh alcohol addition to the recycled alcohol supplied to the reactor where the initial etherification reaction of the tertiary olefin is effected.

Another disadvantage in connection with the production of dialkylether is the necessity of using a more complete distillation installation, in view of the fact that this "undesirable" ether has to be separated from the desired tertiary olefin.

SUMMARY OF THE INVENTION

This invention provides means for avoiding to a large extent the above-mentioned disadvantages. The invention consists of proceeding (a) with at least one catalyst having optimized acidic properties and (b) in the presence of steam.

DETAILED DISCUSSION

The catalyst consists of an alumina (preferably a gamma or eta alumina), generally an activated alumina, to which is added at least one element which, on the one hand, conveniently modifies the acidic properties of the alumina in order to make it more selective in the decomposition of the tertiary ether, and on the other hand, stabilizes the catalytic properties of the alumina as well as its surface, its pore volume and its pore distribution.

The alumina, after incorporation therein of one or more metal elements considered as necessary, and after convenient thermal treatment, has a specific surface from 80 m²/g to 300 m²/g. Preferably the specific surface is from 90 to 280 m²/g and more particularly from 100 to 250 m²/g. As a general rule, the pore volume, after incorporation of the one or more additional metal elements and after convenient thermal treatment, is preferably lower than 0.70 cc/g, the average radius of the pores being preferably in the range from 1 to 10 nanometers and more particularly from 2 to 8 nanometers. (The specific surface of the manufactured catalyst is substantially identical to the specific surface of the alumina used as starting material).

The one or more elements added to the alumina, which are called additional elements or additional agents or also agents for modifying the alumina base, may be introduced by one of the various known methods but it is generally preferred to introduce them by impregnating said alumina with a solution containing the one or more required elements, as salts or as other organic or inorganic derivatives thereof soluble in the selected impregnation solvent.

The selected modifying element is a metal or a metal compound selected from the group consisting of titanium, zirconium and hafnium.

The content by weight, expressed as metal element, of the one or more additional elements deposited on the alumina surface, varies from 0.01% to 5%, preferably from 0.01% to 1% and more particularly, from 0.015 to 0.5% or even from 0.02 to 0.4%, with respect to the alumina.

A method for the preparation of the catalyst consists, for example, as above-specified in impregnating the alumina carrier by means of an aqueous solution (or a solution in a convenient solvent) containing the one or more elements to be introduced, this or these elements being used, for example, as a halide, nitrate, acetate, oxalate, sulfate of a complex containing said one or more elements, for example a complex formed with oxalic acid and oxalates, citric acid and citrates, tartaric acid and tartarates, with other polyacids and alcohol acids and their salts, the acetyl acetonates, etc . . . and any other inorganic or organo-metallic derivative containing said one or more selected elements.

The one or more selected elements being deposited on the alumina, the obtained product is then dried, roasted by heating, for example in a dry air stream (dried by passage, for example, over activated alumina or a molecular sieve, or any other solid having the property of drying air), at a temperature, for example, from 300° to 600° C.

The decomposition reaction of the tert-alkylethers already proceeds with a good yield under atmospheric pressure, but it is generally preferred to conduct the operation under higher pressures, in view of making use of water as cooling agent so as to avoid the requirement of using any other costly technique of heat removal. The operation is preferably conducted under a pressure slightly higher than the vapor pressure of the olefin which it is desired to obtain, at the expected condensation temperature. Thus, it is preferred to proceed under a pressure from 0.11 to 2 MPa and, preferably, from 0.4 to 1 MPa.

The reaction is generally conducted at a temperature from 100° to 500° C., but preferably from 200° to 350° C. The flow rate, expressed in volume of liquid charge per volume of catalyst and per hour (hourly liquid space velocity) ranges from 0.1 to 10 and preferably from 0.7 to 3.

The process of the invention is more particularly useful for the decomposition of tert-butyl-methyl ether to isobutene as shown by equation (2):

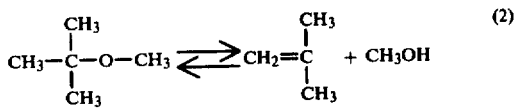

This reaction is generally accompanied by the following parasitic reactions:

(a) the formed methanol dehydrates to dimethyl ether according to reaction (3):

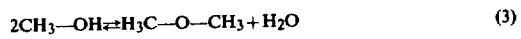

(b) the olefin produced by reaction (2) may dimerize; thus, the obtained isobutene may react according to reaction (4):

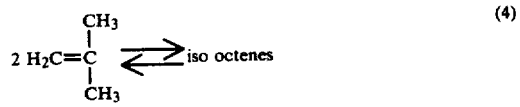

(c) the obtained olefin may also, by reacting with water, be hydrated to produce the corresponding tertiary alcohol.

Thus, in the case of isobutene, tert-butyl alcohol is obtained according to reaction (5):

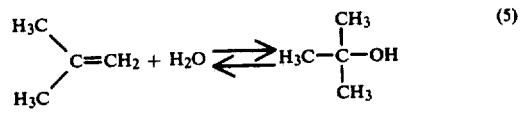

In order to reduce to a minimum the formation of ether, produced by reaction (3), it is convenient, according to the invention, to proceed in the presence of a sufficient amount of steam so as to displace the equilibrium towards the left-hand side of the equation by disfavouring the formation of ether, without however favouring the reaction (5) from the left to the right-hand side of the equation.

The operation is thus effected in the presence, in the reaction medium, of a water amount corresponding to a molar ratio H₂O/tertiary ether from 2 to 8, preferably from 2.5 to 4, at the reactor inlet.

The catalysts and the process described here are particularly adapted to obtain very pure tertiary olefins from the olefinic cuts containing them. The preferred olefinic cuts are those which contain olefinic hydrocarbons having from 4 to 15 carbon atoms per molecule and preferably from 4 to 10. These cuts may be obtained, for example, by catalytic cracking, steam cracking, visbreaking, thermal cracking, etc.

Examples of the various olefins which can be obtained in a pure state in conformity with the invention, are: isobutene, isoamylenes such as 2-methyl-1-butene and 2-methyl-2-butane, iso-hexenes such as 2,3-dimethyl-1-butene, 2,3-dimethyl-2-butene, 2-methyl-2-pentene, 2-methyl-1-pentene, 3-methyl-2-pentene (cis and trans), 2-ethyl-1-butene, 1-methyl-cyclopentene, tertiary heptenes, etc.

The reaction of decomposition of the tertiary ethers to primary alcohols and to so-called tertiary olefins is substantially quantitative.

This reaction, effected in the presence of a conveniently selected catalyst, does not produce or produces only to a small extent dimers and trimers of the obtained tertiary olefin and also does not produce, or produces only to a small extent, tertiary alcohol.

The present invention is illustrated by the following nonlimitative examples.

All the catalysts used in these experiments were in the form of balls having a diameter of 1 to 3 mm and previously roasted at 450° C. before use.

EXAMPLE 1 (COMPARATIVE)

For the decomposition of methyl tert-butyl ether (MTBE) there was used a catalyst A, free of additional agent, consisting of 100 g of alumina having the following characteristics:

| | |
|---|---|
| Specific surface | 200 m$^2$/g |
| Pore volume | 0.59 cc/g |
| The operating conditions were as follows | |
| Temperature of the reactor | 265° C. |
| Pressure | 0.6 MPa |
| pph of MTBE (space velocity) | 1.48 |
| pph of water (space velocity) | 0.9 | molar ratio $\frac{H_2O}{MTBE} = 3$ (at the reactor input)

pph = weight of material per unit by weight of catalyst and per hour.

There is introduced into the reactor, per hour, 148 g of MTBE and 90 g of water, i.e. a total of 238 g. The weight of the product at the output of the reactor was also 238 g.

There is thus recovered, at the output, the entirety by weight of what was introduced.

The composition of the product at the output of the reactor was, in % by weight:

| | | |
|---|---|---|
| MTBE | 1.24 | |
| isobutene (isobutylene) | 38.40 | |
| Tert butyl alcohol | 0.51 | 62.09% |
| Methanol | 21.39 | |
| Dimethyl ether | 0.55 | |
| Water | 37.91 | |
| Σ Isooctenes | 0.0 | |
| | 100 | |

EXAMPLE 2 (COMPARATIVE)

The catalyst B, used in this example, and which is also free of additional agent, is an alumina having a too low specific surface of 55 m$^2$/g and a pore volume of 0.51 cc/g.

The operating conditions are the same as in example 1.

The composition of the product obtained at the output of the reactor was in % by weight:

| | | |
|---|---|---|
| MTBE | 29.85 | |
| Isobutene | 19.55 | |
| Tert butyl alcohol | 1.35 | 62.45 |
| Methanol | 11.53 | |
| Dimethyl ether | 0.17 | |
| Water | 37.55 | |
| Σ iso-octenes | 0 | |
| | 100 | |

EXAMPLE 3 (COMPARATIVE)

In this example, the alumina used as catalyst C (also free of additional agent) had a too high specific surface of 450 m$^2$/g and a pore volume of 0.52 cc/g. The operating conditions were identical to those of examples 1 and 2.

The effluent of the reactor had the following composition in % by weight:

| | | |
|---|---|---|
| MTBE | 1.24 | |
| Isobutene | 33.74 | |
| Tert butyl alcohol | 0.52 | 62.06 |
| Methanol | 21.27 | |
| Dimethyl ether | 0.64 | |
| Σ iso-octenes | 4.65 | |
| Water | 37.94 | |
| | 100 | |

In Table I below, there is reported, for examples No. 1 to 3, the molar conversion of MTBE, the molar yield of the recovered isobutylene with respect to the converted MTBE and the molar percent of the produced methanol.

TABLE I

| EXAMPLE | CATALYST | ALUMINA S m$^2$/g | CONVERSION of MTBE % MOLAR | RECOVERED ISOBUTYLENE % MOLAR | RECOVERED METHANOL % MOLAR |
|---|---|---|---|---|---|
| 1 | A | 200 | 98 | 99 | 96.5 |
| 2 | B | 55 | 52.2 | 95 | 98 |
| 3 | C | 450 | 98 | 98 | 96 |

The results obtained in example 2 show the lack of selectivity but above all, of activity, of the catalyst, which is the result in this case of the low specific surface of the alumina used.

An increase of the reaction temperature in order to compensate for the insufficient activity cannot be contemplated since it would result in the formation of important secondary reactions.

EXAMPLE 4

The catalysts D, E and F, used in this example according to this invention, are the catalysts obtained from the alumina used in example 1 but with the addition of an acidity modulating agent, i.e. zirconium for catalyst D, titanium for catalyst E, hafnium for catalyst F.

The catalysts have been prepared by adding to 100 g of said alumina of example 1:
  60 cc of an aqueous solution containing 2 g of zirconyl acetate solution at a 10% zirconium content, for catalyst D, 4.3 g of titanium trichloride solution containing 15% by weight of trichloride, for catalyst E, and 2 g of aqueous solution of hafnium oxychloride containing 10% by weight of hafnium, for catalyst F.

The contact is maintained for 4 hours, and then the mixture is drained and dried while progressively increasing the temperature up to 100° C., for 1 hour, then maintained at this temperature for 1 hour and then roasted at 450° C. in dry air for 2 hours.

The so-obtained catalysts D, E and F contain, by weight:

| Catalyst D: | 0.2% of zirconium |
|---|---|
| Catalyst E: | 0.2% of titanium |
| Catalyst F: | 0.2% of hafnium |

The specific surface and pore volume of these catalysts D, E and F are substantially identical of those of the catalyst A, i.e. respectively 200 m²/g and 0.59 cc/g.

The operating conditions and the charge are the same as in example 1.

The results are reported in Table II below:

TABLE II

| COMPOSITION OF THE PRODUCT | CATALYST | | |
|---|---|---|---|
| in % by weight | D | E | F |
| MTBE | 1.24 | 1.24 | 1.25 |
| Isobutene | 38.74 | 38.75 | 38.72 |
| Tert. Butanol | 0.05 | 0.04 | 0.04 |
| Methanol | 21.95 | 21.72 | 21.83 |
| Dimethyl ether | 0.16 | 0.32 | 0.26 |
| Water | 37.86 | 37.93 | 37.90 |
| Isooctene | 0. | 0. | 0. |
| Converted MTBE (%) | 98.0 | 98.0 | 98.0 |
| Yield of recovered isobutene (%) | 99.9 | 99.9 | 99.9 |
| Recovered methanol (%) | 99.0 | 98.1 | 98.6 |

EXAMPLE 5

A series of tests is effected with the catalysts prepared as indicated in example 4 but with various contents of metal elements. The results are given in Table III.

The conditions of the tests are still the same as those used in the preceding examples, the specific surface of these catalysts being 200 m²/g and the pore volume being 0.59 cc/g in the catalysts G to O.

TABLE III

| CATALYST | CONTENT OF METALLIC ELEMENT (expressed as metal) | CONVERTED MTBE (%) | YIELD OF RECOVERED ISOBUTENE (%) | RECOVERED METHANOL (%) |
|---|---|---|---|---|
| G | 0.009% Ti | 98 | 99.0 | 96.5 |
| H | 0.02% Ti | 98 | 99.2 | 97.5 |
| I | 0.6% Ti | 93 | 98.2 | 98 |
| J | 0.009% Zr | 98.0 | 99.0 | 96.5 |
| K | 0.02% Zr | 98.0 | 99.3 | 98.4 |
| L | 0.6% Zr | 94 | 97.1 | 97 |
| M | 0.009% Hf | 98.0 | 99.0 | 96.5 |
| N | 0.02% Hf | 98.0 | 99.1 | 97.8 |
| O | 0.6% Hf | 93.5 | 97.6 | 97.3 |

These results show that the selectivities obtained with catalysts H, K and N conforming with the invention, are acceptable although lower than those obtained with the catalysts D, E and F whose content of metal element is more adequate. These results also show, on the one hand, the decrease in activity resulting from the use of catalysts I, L and O whose content of metallic element is slightly too high and, on the other hand, the inefficiency of a too low content of metallic element as in catalysts G, J and M, not conforming with the invention.

EXAMPLE 6 (COMPARATIVE)

Example 4 is repeated with catalysts D, E and F, but while proceeding in the absence of steam.

The obtained results are indicated in Table IV.

TABLE IV

| CATALYST | D | E | F |
|---|---|---|---|
| Converted MTBE (%) | 100 | 100 | 100 |
| Recovered isobutene (%) | 94 | 95 | 94 |
| Recovered methanol (%) | 64 | 58 | 60 |

EXAMPLE 7 (COMPARATIVE)

Example 4 is repeated but with the use of the same alumina as in example 2, having a specific surface of 55 m²/g. The results obtained are indicated in Table V. The specific surface of the modified catalysts D, E and F is 55 m²/g, the pore volume being 0.51 cc/g.

TABLE V

| CATALYST | MODIFIED D | MODIFIED E | MODIFIED F |
|---|---|---|---|
| Converted MTBE | 63 | 63 | 63 |
| Recovered isobutene (%) | 97 | 97.1 | 96.8 |
| Recovered methanol (%) | 97.8 | 97.1 | 97.4 |

What is claimed is:

1. A process for producing a tertiary olefin of the formula:

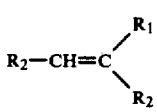

by decomposition of the corresponding tertiary ether of the formula:

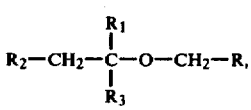

wherein $R_1$ and $R_3$ are each independently an alkyl, arylalkyl, aryl or alkylaryl radical; and $R_2$ and R are each independently a hydrogen atom or an alkyl, arylalkyl, aryl or alkylaryl radical, said process comprising the step of contacting said ether, in the presence of steam, the molar ratio H$_2$O/tertiary ether being from 2 to 8, with a catalyst consisting essentially of alumina having deposited thereon at least one modifying agent, said agent being titanium, zirconium or hafnium, as the elemental metal or a metal compound, the content of said metal or metal compound, expressed as the elemental metal, being 0.01–5% by weight with respect to the alumina, said alumina, after incorporation of the metal or metal compound, having a specific surface of 80–300 m$^2$/g; whereby the tertiary olefin is produced in high purity, and parasitic side-reactions which decrease the yields of tertiary olefin and of recovered alcohol are minimized.

2. A process according to claim 1, wherein the specific surface of the alumina is from 100 to 250 m$^2$/g.

3. A process according to claim 1, conducted under a pressure of from 0.11 to 2 MPa, at a temperature of from 100° to 500° C., with an hourly liquid space velocity of from 0.1 to 10 volumes of liquid charge per volume of catalyst and per hour, the molar ratio H$_2$O/tertiary ether being from 2.5 to 4.

4. A process according to claim 3, wherein the pressure is from 0.4 to 1 MPa, the temperature from 200° to 350° C. and the space velocity from 0.7 to 3.

5. A process according to claim 1, wherein the content of metal or metal compound, expressed as metal element, is from 0.01 to 1% by weight with respect to the alumina.

6. A process according to claim 5, wherein said content is from 0.015 to 0.5%.

7. A process according to claim 1, wherein said agent is titanium or a titanium compound.

8. A process according to claim 1, wherein said agent is zirconium or a zirconium compound.

9. A process according to claim 1, wherein said agent is hafnium or a hafnium compound.

10. A process according to claim 1, wherein the starting tertiary ether is the product obtained by treating an olefinic cut containing the desired tertiary olefin, with an alcohol, to produce the tertiary ether corresponding to the desired tertiary olefin, and then separating said tertiary ether by distillation.

11. A process according to claim 1, wherein said tertiary ether is methyl tert-butyl ether, and said tertiary olefin is isobutene.

12. A process according to claim 1, wherein said tertiary olefin is an isoamylene, an isohexene, a tertiary heptene or 1-methylcyclopentene.

13. A process according to claim 1, wherein R$_1$ and R$_3$ are each an alkyl radical, and R$_2$ and R are each a hydrogen atom or an alkyl radical.

14. A process according to claim 11, wherein the specific surface of the alumina is from 100 to 250 m$^2$/g.

15. A process according to claim 11, conducted under a pressure of from 0.11 to 2 MPa, at a temperature of from 100° to 500° C., with an hourly liquid space velocity of from 0.1 to 10 volumes of liquid charge per volume of catalyst and per hour, the molar ratio H$_2$O/tertiary ether being from 2.5 to 4.

16. A process according to claim 15, wherein the pressure is from 0.4 to 1 MPa, the temperature from 200° to 350° C. and the space velocity from 0.7 to 3.

17. A process according to claim 11, wherein the content of metal or metal compound, expressed as metal element, is from 0.01 to 1% by weight with respect to the alumina.

18. A process according to claim 17, wherein said content is from 0.015 to 0.5%.

19. A process according to claim 11, wherein said agent is titanium or a titanium compound.

20. A process according to claim 11, wherein said agent is zirconium or a zirconium compound.

21. A process according to claim 11, wherein said agent is hafnium or a hafnium compound.

22. A process according to claim 11, wherein the starting methyl tert-butyl ether is obtained by treating a C$_4$ olefinic cut containing isobutene with methanol, and separating the resultant methyl tert-butyl ether by distillation.

* * * * *